United States Patent
Takakura et al.

(10) Patent No.: US 7,524,876 B2
(45) Date of Patent: Apr. 28, 2009

(54) LUCIFERIN DERIVATIVES

(75) Inventors: Hideo Takakura, Aichi (JP); Yasuteru Urano, Kanagawa (JP); Tetsuo Nagano, Tokyo (JP)

(73) Assignee: The University of Tokyo, Tokyo (JP)

( * ) Notice: Subject to any disclaimer, the term of this patent is extended or adjusted under 35 U.S.C. 154(b) by 353 days.

(21) Appl. No.: 11/493,815

(22) Filed: Jul. 27, 2006

(65) Prior Publication Data
US 2007/0155806 A1    Jul. 5, 2007

(30) Foreign Application Priority Data
Sep. 30, 2005    (JP)    ............... P2005-286948

(51) Int. Cl.
*A61K 31/428*    (2006.01)
*C07D 277/62*    (2006.01)
*C07D 417/04*    (2006.01)

(52) U.S. Cl. .................. 514/367; 548/146; 548/152; 548/178; 514/365

(58) Field of Classification Search ................ 548/146, 548/152, 178; 514/365, 367
See application file for complete search history.

(56) References Cited
U.S. PATENT DOCUMENTS 5,035,999 A * 7/1991 Geiger et al. ................ 435/23
7,148,030 B2 * 12/2006 O'Brien et al. ................ 435/8

FOREIGN PATENT DOCUMENTS
JP    2000-270894    10/2000

OTHER PUBLICATIONS

English language Abstract of JP 2000-270894.

Miska et al. "Synthesis and Characterization of Luciferin Derivatives for Use in Bioluminescence Enhanced Enzymen Immunoassays", Journal of Clinical Chemistry and Clinical Biochemistry, vol. 25, No. 1, 1987, pp. 25-30.

* cited by examiner

*Primary Examiner*—Golam M Shameem
(74) *Attorney, Agent, or Firm*—Greenblum & Bernstein, P.L.C.

(57) ABSTRACT

A compound represented by the following general formula (I) or a salt thereof:

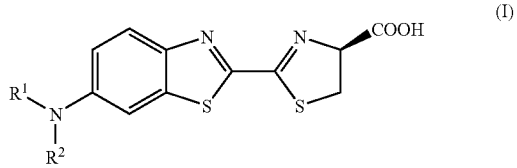

[wherein $R^1$ and $R^2$ represent hydrogen atom, a $C_{1-6}$ alkyl group, or a group represented by the following formula (A):

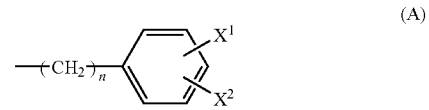

[wherein $X^1$ and $X^2$ represent hydrogen atom, or a group represented as —N($R^3$)($R^4$) ($R^3$ and $R^4$ represent hydrogen atom, a $C_{1-6}$ alkyl group, a $C_{1-6}$ alkylcarbonyl group, or a $C_{1-6}$ alkyloxycarbonyl group); and n represents an integer of 1 to 6 ], provided that $R^1$ and $R^2$ do not simultaneously represent hydrogen atom), which is a novel luciferin derivative that serves as a luciferase substrate.

5 Claims, 2 Drawing Sheets

LUCIFERIN DERIVATIVES

TECHNICAL FIELD

The present invention relates to a novel luciferin derivative that can serve as a luciferase substrate.

BACKGROUND ART

Bioluminescence method utilizing bioluminescence produced by a combination of firefly luciferase and a luciferin does not require excitation light, and accordingly produces substantially no background noise to achieve highly sensitive measurement. Further, since the method does not require excitation light, measurements can be conducted by using an apparatus with a simple structure. Due to these characteristic features, the bioluminescence method is widely used to detect target substances in blotting, reporter enzymes for various assay systems and the like. Furthermore, the method also enables imaging of deep portions of a biological sample having poor light transmission, and therefore, applications of the method to in vivo imaging systems have recently been being studied.

The bioluminescence method is believed to be effective in in viva imaging as described above. However, since the emission wavelength in the conventional bioluminescence method is limited to 570 nm as that of luciferin, a problem arises that the wavelength is too short for use in in vivo imaging. Therefore, researches have been made to shift the emission wavelength to a longer side to achieve superior tissue transmission. However, most of these researches have been conducted by modifying characteristic features of luciferase as an enzyme, so there is almost no report whose approach is to modify luciferin as substrates.

On the other hand, although sensitivity of the bioluminescence method have been mainly focused on, some reports are directed to studies on functional luciferase substrates that enable on/off control of the bioluminescent feature so that luminescence is generated only in the presence of a target molecule (for example, Japanese Patent Laid-Open Publication (Kokai) No. 2000-270894; Miska, W., Geiger, R., J. Clin. Chem. Clin. Biochem., January; 25(1) pp.23-30, 1987, etc.). These studies relate to on/off control type luminescent probes using luciferin and analogues thereof, which utilize the feature that methyl ether-type luciferin or amide-type aminoluciferin does not show luminescence, and are based on the principle of detecting activity of an enzyme that specifically reacts with a sugar or a peptide that binds to these luciferin analogues beforehand. However, this principle has a problem that applicable targets of probes are very limited. Therefore, it has been desired to develop a widely applicable bioluminescent probe that enables functional luminescence imaging in vivo.

DISCLOSURE OF THE INVENTION

An object of the present invention is to provide a compound as a luciferin derivative which has a structure that can be a luciferase substrate, and has a unique luminescence feature such as a compound with an emission wavelength longer than that of a luciferin or a non-luminescent compound. Further, another object of the present invention is to provide a luciferin derivative which, per se, is non-luminescent, but changes into a luminescent substrate due to molecular structural alteration thereof in the presence of a target molecule.

The inventors of the present invention conducted various researches to achieve the foregoing objects. As a result, they found that a luciferin derivative, exhibiting strong luminescence. similar to that of a luciferin and having an emission wavelength significantly shifted to a long wavelength side compared with that of a luciferin, was successfully provided by alkylation of the amino group of aminoluciferin, and that the resulting luciferin derivative was extremely useful for in vivo imaging. They also found that a compound obtained by introducing aminobenzyl group to aminoluciferin did not lose the characteristic of being a luciferase substrate, but was still non-luminescent even after the reaction as a substrate, and that a compound obtained by acylating the amino group of said compound maintained the characteristic of being a luciferase substrate and generated strong luminescence by reaction with luciferase. The present invention was accomplished on the basis of the aforementioned findings.

The present invention thus provides a compound represented by the following general formula (I):

[wherein $R^1$ and $R^2$ independently represent hydrogen atom, a $C_{1-6}$ alkyl group which may be substituted, or a group represented by the following formula (A):

[wherein $X^1$ and $X^2$ independently represent hydrogen atom, or a group represented as $-N(R^3)(R^4)$ (wherein $R^3$ and $R^4$ independently represent hydrogen atom, a $C_{1-6}$ alkyl group which may be substituted, a $C_{1-6}$ alkylcarbonyl group which may be substituted, or a $C_{1-6}$ alkyloxycarbonyl group which may be substituted); and n represents an integer of 1 to 6]), provided that $R^1$ and $R^2$ do not simultaneously represent hydrogen atom], or a salt thereof As a preferred embodiment of the aforementioned invention, provided is the compound or a salt thereof, wherein, in the aforementioned general formula (I), at least one of $R^1$ and $R^2$ is a $C_{1-6}$ alkyl group. According to a preferred embodiment of this invention, there is provided the aforementioned compound or a salt thereof, wherein at least one of $R^1$ and $R^2$ is methyl group.

Further, according to another preferred embodiment of the aforementioned invention, provided is the compound or a salt thereof, wherein, in the aforementioned general formula (I), $R^1$ is hydrogen atom, and $R^2$ is a group represented by the formula (A) (wherein $X^1$ and $X^2$ both represent hydrogen atom; and n represents an integer of 1 to 6). According to a preferred embodiment of this invention, there is provided the aforementioned compound or a salt thereof, wherein n is 1 to 3.

Further, according to another preferred embodiment of the aforementioned invention, provided is the compound or a salt thereof, wherein, in the general formula (I), $R^1$ is hydrogen atom, and $R^2$ is a group represented by the formula (A)

[wherein $X^1$ is hydrogen atom, $X^2$ is a group represented as —N($R^3$)($R^4$) (wherein $R^3$ and $R^4$ independently represent hydrogen atom, a $C_{1-6}$ alkyl group which may be substituted, a $C_{1-6}$ alkylcarbonyl group which may be substituted, or a $C_{1-6}$ alkyloxycarbonyl group which may be substituted); and n represents an integer of 1 to 6]. According to a preferred embodiment of this invention, provided are the aforementioned compound or a salt thereof, wherein $R^3$ and $R^4$ are hydrogen atoms, and n is 2; and the aforementioned compound or a salt thereof, wherein either one of $R^3$ and $R^4$ is hydrogen atom, the other is benzyloxycarbonyl group, and n is 2. More preferably, there is provided the aforementioned compound or a salt thereof, wherein $X^2$ binds at the para-position.

From another aspect of the present invention, there is provided a luciferase substrate comprising a compound represented by the aforementioned general formula (I) or a salt thereof. The present invention also provides an agent for bioluminescence analysis comprising a compound represented by the aforementioned general formula (I) or a salt thereof, which generates luminescence by a reaction with a luciferase. The present invention also provides a bioluminescence assay method comprising the step of reacting a luciferase with a biological sample labeled with the aforementioned compound represented by the general formula (I) or a salt thereof, which generates luminescence by a reaction with the luciferase. The present invention further provides a bioluminescence analysis kit comprising the aforementioned agent for bioluminescence analysis and a luciferase as components.

The compound or a salt thereof provided by the present invention has a characteristic feature that can be luciferase substrate. The compound of the present invention or a salt thereof having a luminescent property has an emission wavelength shifted to a longer wavelength side compared with that of a luciferin and is useful for in vivo imaging or as a luminescence labeling agent. Further, the compound of the present invention or a salt thereof, which is substantially non-luminescent even after the reaction as a substrate of a luciferase, can be preferably used as a fundamental skeleton of a luminescent probe that generates luminescence only after reaction as a substrate of a luciferase in the presence of a target molecule.

BEST MODE FOR CARRYING OUT THE INVENTION

In the present specification, "alkyl group" or alkyl moiety of a substituent containing the alkyl moiety (for example, alkylcarbonyl group and the like) means a saturated hydrocarbon group having a straight, branched or cyclic chain or any combination thereof. More specifically, examples of the alkyl group include methyl group, ethyl group, n-propyl group, isopropyl group, cyclopropyl group, n-butyl group, sec-butyl group, isobutyl group, tert-butyl group, cyclopropylmethyl group, n-pentyl group, n-hexyl group, and the like.

In the present specification, when a certain functional group is referred to with the expression "which may be substituted", type and number of substituents and the substitution positions thereof are not particularly limited, and the functional group may have, for example, an alkyl group, a halogen atom (which may be any of fluorine atom, chlorine atom, bromine atom and iodine atom), hydroxyl group, amino group, carboxyl group, sulfonic acid group, an alkylsulfonate group, or the like as the substituents. Further, in the present specification, aryl group may be a monocyclic or polycyclic aryl group, and a phenyl group can be preferably used. The same shall apply to aryl ring, and a benzene ring can be preferably used.

In the aforementioned general formula (I), it is preferred that either of $R^1$ and $R^2$ is hydrogen atom, and the other is a $C_{1-6}$ alkyl group which may be substituted, and it is also preferred that $R^1$ and $R^2$ both are $C_{1-6}$ alkyl groups which may be substituted. When the $C_{1-6}$ alkyl group represented by $R^1$ or $R^2$ has a substituent, the substituent is preferably an aryl group which may be substituted or a heteroaryl group which may be substituted. It is also preferred that the $C_{1-6}$ alkyl group which may be substituted is a straight $C_{1-6}$ alkyl group. It is particularly preferred that $R^1$ and $R^2$ both are methyl groups.

Further, in the aforementioned general formula (I), it is also preferred that either of $R^1$ and $R^2$ is hydrogen atom, and the other is a group represented by the formula (A). In the aforementioned embodiment, (a) it is more preferred that $X^1$ and $X^2$ both are hydrogen atoms, and n is an integer of 1 to 6 in the formula (A). It is particularly preferred that n is 1 to 3, more specifically, it is particularly preferred that the group represented by the formula (A) is benzyl group, phenethyl group or 3-phenylpropyl group. The compound or a salt thereof of this embodiment has a structure that can be a luciferase substrate, and is characterized in that it generates luminescence at a wavelength 15 to 30 nm longer than that of aminoluciferin (known to have an emission wavelength longer than that of luciferin) after reaction as a substrate of a luciferase.

(b) it is preferred that, in the formula (A), $X^1$ is hydrogen atom, and $X^2$ is a group represented as —N($R^3$)($R^4$), wherein $R^3$ and $R^4$ independently represent hydrogen atom or a $C_{1-6}$ alkyl group which may be substituted (provided that when $R^3$ and $R^4$ have a substituent, those compounds wherein the substituted alkyl group is a $C_{1-6}$ alkylcarbonyl group which may be substituted, or a $C_{1-6}$ alkyloxycarbonyl group which may be substituted are excluded). It is preferred that $R^3$ and $R^4$ both are hydrogen atoms, and it is preferred that $X^2$ binds to the para-position. The compound or a salt thereof of this embodiment has a structure that can be a substrate of a luciferase, and has a property that when it reacts as a substrate of a luciferase, electrons are donated from the benzene ring moiety having a high electron density (high HOMO energy) to the aminoluciferin moiety as the luminescence site, and thus it does not generate luminescence.

(c) it is preferred that, in the formula (A), $X^1$ is hydrogen atom, and $X^2$ is a group represented as —N($R^3$)($R^4$), wherein either of $R^3$ and $R^4$ is hydrogen atom, and the other is a $C_{1-6}$ alkylcarbonyl group which may be substituted, or a $C_{1-6}$ alkyloxycarbonyl group which may be substituted. Preferred examples of the $C_{1-6}$ alkylcarbonyl group which may be substituted represented by $R^3$ or $R^4$ include, for example, acetyl group. Preferred examples of the $C_{1-6}$ alkyloxycarbonyl group which may be substituted represented by $R^3$ or $R^4$ include, for example, benzyloxycarbonyl group. The compound or a salt thereof according to this embodiment has a structure that can be a luciferase substrate and is characterized in that, when it reacts as a luciferase substrate, it generates luminescence at a wavelength longer than that of aminoluciferin.

Therefore, the compound or a salt thereof according to the aforementioned embodiment (a) or (c) is preferred as a luminescence labeling agent for amino acids, oligopeptides, polypeptides (including proteins), and the like. The means for binding these compounds or salts thereof to carboxyl group or amino group of an amino acid or the like are well known to those skilled in the art, and suitable methods can be selected. For example, means such as crosslinking agents described in the catalog of PIERCE, "Applications Handbook and Catalog 2005/2006," Section 9, and the like can be used. Further, the compound or a salt thereof according to the aforementioned embodiment (b) has a property that the substance is chemically modified by a transferase such as acyltransferase so that either of $R^3$ and $R^4$ changes into a $C_{1-6}$ alkylcarbonyl group which may be substituted, and thus changes into a luminescent compound or a salt thereof. In the specification, the term "luminescent property" means a property of generating luminescence by a reaction with luciferase. Also in the specification, the expression that the compound of the present invention is "non-luminescent" means that the compound can serve as a luciferase substrate, but the resultant of the enzymatic reaction generates substantially no luminescence.

The compound of the present invention represented by the aforementioned general formula (I) can exist as an acid addition salt or a base addition salt. Examples of the acid addition salt include mineral acid salts such as hydrochlorides, sulfates and nitrates, organic acid salts such as methanesulfonates, p-toluenesulfonates, oxalates, citrates and tartrates, and the like. Examples of the base addition salt include metal salts such as sodium salts, potassium salts, calcium salts and magnesium salts, ammonium salts, organic amine salts such as triethylamine salts, and the like. In addition to these examples, the compound may form a salt with an amino acid such as glycine. The compound of the present invention or a salt thereof may also exist as a hydrate or a solvate, and these substances all fall within the scope of the present invention.

The compound of the present invention represented by the aforementioned general formula (I) may have one or more than one asymmetric carbons depending on the type of substituent. Optically active substances based on one or more than one asymmetric carbons and stereoisomers such as diastereoisomers based on two or more asymmetric carbons, as well as arbitrary mixtures of stereoisomers, racemates, and the like fall within the scope of the present invention.

Methods for producing typical compounds of the present invention are specifically explained in the examples of the present specification. Therefore, in view of those explanations, those skilled in the art can suitably select starting materials, reaction conditions, reagents and the like and prepare any of the compounds of the present invention represented by the aforementioned general formula (I) by optionally modifying or altering those methods.

Luminescence of the luciferin-luciferase system is generated by a reaction in which D-luciferin as the substrate is oxidized to oxyluciferin as a luminescent compound by luciferase in the presence of ATP and $Mg^{2+}$. Since luminescence is rapidly attenuated, a luminometer equipped with an autoinjector was conventionally required. However, more intense and stable luminescence can currently be obtained by an improved method utilizing addition of coenzyme A (CoA) (Promega Protocols and Application Guide, 2nd edition), and any special apparatus is no longer required.

Luciferin $$ATP + O_2 \xrightarrow{\text{Luciferase}}_{Mg^{2+}}$$

Oxyluciferin $$AMP + CO_2 + \text{Light}$$

Since the bioluminescence method utilizing bioluminescence generated by the combination of firefly luciferase and a luciferin does not require excitation light so as to completely avoid background noise, unlike fluorescence methods, and the method requires only a simple measurement apparatus. Therefore, the method has been used in various ways in the filed of analytical chemistry including clinical tests and hygiene inspections. Further, by using this luminescence system in vivo, adenosine triphosphate (ATP) or the like can be detected absolutely without being affected by the background noise due to enzymes in the host cells. In addition, it is widely applied to reporter gene assays in which luciferase activity is detected as a reporter protein. The compound of the present invention or a salt thereof can serve as a luciferase substrate, and has a property that the substance is oxidized to a corresponding oxyluciferin derivative by the luciferase in the presence of ATP and $Mg^{2+}$. As explained above, the compound of the present invention or a salt thereof becomes either luminescent or non-luminescent after the reaction by luciferase depending on the structure of the compound. Whether the compound of the present invention generates luminescence after the reaction by luciferase can be easily confirmed by those skilled in the art by using the method described in the examples of the present specification.

When the compound of the present invention or a salt thereof is used as a luciferase substrate, a compound represented by the aforementioned general formula (I) or a salt thereof per se may be used, or it can be mixed with additives ordinarily used for preparation of agents and used as a composition, if necessary. For example, as additives for agents used in a physiological environment, additives such as dissolving aids, pH modifiers, buffers and isotonic agents can be used, and amounts of these additives can be suitably selected by those skilled in the art. Such a composition is provided as a composition in an appropriate form such as powdery mixture, lyophilized product, granule, tablet and solution.

For example, the compound of the present invention or a salt thereof can be used as a luminescence labeling agent. Types of substances to be labeled are not particularly limited, and examples thereof include biological molecules such as proteins, nucleic acids, lipids as well as various organic low molecular compounds and organic macromolecular compounds. The labeling method is not particularly limited, and labeling can be performed according to labeling methods using conventional luminescence labeling agents, fluorescence labeling agents, and the like.

Further, in recent years, detection of a trace amount of luciferase luminescence in the body (in vivo), which was conventionally difficult, has become possible with advancement of CCD cameras and image analysis techniques. By administering the luminescent luciferase substrate of the present invention to cells (cancer cells, bacteria and the like), into which a luciferase gene is introduced, or intraperitoneally administering them to transgenic mice, disease model animals or the like, into which a luciferase gene is introduced, a prolonged in vivo imaging of expression of genes and proteins, changes in expression of efficacy of medicaments over time and the like becomes possible. Although attempts of using luciferins for this purpose have been conventionally known, they have a drawback that the wavelength of luminescence generated by luciferins is 570 nm, which leads to low tissue transmission. The luminescent compound of the present invention has a property of generating luminescence at a wavelength of 610 nm or longer achieving high tissue transmission, and when the compound is applied to in vivo imaging, more favorable measurement results can be obtained compared with luciferins.

It is conventionally known that methyl ether type luciferin and amide type aminoluciferin do not serve as a luciferase substrate and do not generate luminescence. By utilizing this property, an attempt was made to bind a sugar or a peptide to a luciferin or aminoluciferin (these are compounds generating luminescence by luciferase) via the ether bond or amide bond to prepare a compound which per se is non-luminescent and does not serve as a luciferase substrate, and to use such compound as an agent to detect an enzyme, on the basis of luminescence, that specifically reacts with the compound to produce luciferin or aminoluciferin. However, the aforementioned compounds used in this method per se do not serve as a luciferase substrate. On the contrary, the non-luminescent compound of the present invention or a salt thereof per se has a property of serving as a luciferase substrate and is converted to a luminescent luciferase substrate by an action of an enzyme to be detected. For example, the non-luminescent compound of the aforementioned embodiment (b) can be used as a probe for detection of acyltransferase. More specifically, an alkylamino group in this compound or a salt thereof is converted to an alkylcarbonylamino group in the presence of acyltransferase, and this compound (compound of the aforementioned embodiment (c)) generates luminescence by the reaction with luciferase. On the other hand, the compound keeps non-luminescent in the absence of acyltransferase even after the reaction with the luciferase. Therefore, the presence or absence of acyltransferase can be proved by the presence or absence of luminescence.

EXAMPLES

The present invention will be explained more specifically with reference to examples. However, the scope of the present invention is not limited to the following examples.

Example 1

Synthesis of Aminoluciferin derivatives 10 to 14

The synthetic scheme of Compounds 10 to 14 is shown below.

(A) Synthesis of 2-chloro-6-nitrobenzothiazole (2)

Compound 1 (25.1 g, 147 mmol) was added dropwise to concentrated sulfuric acid (135 mL) under ice cooling, then potassium nitrate (16.4 g, 162 mmol) was added to the mixture. The mixture was stirred under ice cooling as it was for 30 minutes, and then stirred at room temperature for 1 hour. The reaction mixture was poured into ice water, and the precipitates were separated by filtration and washed with water. The precipitates were recrystallized from ethanol to obtain Compound 2 as white acicular crystals (15.6 g, 49% yield).

$^1$H-NMR (300 MHz, CDCl$_3$) δ 8.07 (d, 1H, J=8.9 Hz), 8.39 (dd, 1H, J=2.2, 8.9 Hz) 8.75 (d, 1H, J=2.2 Hz). MS (EI$^+$) 214, M$^+$.

(B) Synthesis of 2-chloro-6-aminobenzothiazole (3)

Compound 2 (1.96 g, 9.14 mmol) was dissolved in ethanol (150 mL) and purified water (100 mL), and the solution was added with anhydrous tin(II) chloride (20.7 g, 91.7 mmol). The mixture was added with 4.8 mol/L hydrochloric acid (20 mL, 96 mmol) and refluxed at 120° C. After disappearance of the starting materials was confirmed by thin layer chromatography (developing solvent: dichloromethane), the mixture was basified with aqueous sodium hydroxide. The precipitates were removed by filtration, After, ethanol was evaporated, the residue was extracted three times with ethyl acetate. Then organic layer was washed with saturated brine, dried over anhydrous sodium sulfate, and concentrated under reduced pressure. The residue was purified by silica gel column chromatography (developing solvent: ethyl acetate/n-hexane=1/1) to obtain Compound 3 as white solid (1.02 g, 61% yield).

$^1$H-NMR (300 MHz, CDCl$_3$) δ 3.85 (br, 2H), 6.81 (dd, 1H, J=2.4, 8.7 Hz), 6.99 (d, 1H, J=2.4 Hz), 7.70 (d, 1H, J=8.7 Hz). MS (ESI$^+$) 185.0, [M+H]$^+$.

(C) Synthesis of 2-cyano-6-aminobenzothiazole (4)

Potassium cyanide (1.29 g, 19.7 mmol) was added to dimethyl sulfoxide (DMSO, 150 mL). After argon substitution, the mixture was refluxed overnight at 135° C. with stirring. The temperature was lowered to 120° C., and Compound 3 (1.02 g, 5.55 mmol) dissolved in DMSO (20 mL) was added. After disappearance of the starting materials was confirmed by thin layer chromatography (developing solvent: ethyl acetate/n-hexane=2/1), the reaction mixture was poured into a mixed solution of 1.0 mol/L potassium dihydrogenphosphate solution (100 mL) and diethyl ether, (150 mL), and the diethyl ether layer was separated. The aqueous layer was extracted 5 times with ethyl acetate, the organic layer was mixed with the diethyl ether layer, and this organic solvent layer was washed twice with purified water and twice with saturated brine. The organic layer was dried over anhydrous sodium sulfate and concentrated under reduced pressure. The residue was purified by silica gel column chromatography (developing solvent: ethyl acetate/n-hexane=1/4 to 1/2) to obtain Compound 4 as yellow solid (521 mg, 54% yield).

$^1$H-NMR (300 MHz, CDCl$_3$) δ 4.13 (br, 2H), 6.96 (dd, 1H, J=2.4, 8.9 Hz), 7.09 (d, 1H, J=2.4 Hz), 7.95 (d, 1H, J=8.9 Hz). MS (ESI$^+$) 176.0, [M+H]$^+$.

(D) Synthesis of 2-cyano-6-methylaminobenzothiazole (5)

Formaldehyde (37% (v/v), 48 mg, 0.60 mmol) dissolved in tetrahydrofuran (THF, 20 mL) was added with 180 mmol/L sulfuric acid (3.2 mL, 0.6 mmol), and stirred at room temperature for several minutes. Compound 4 (99 mg, 0.57 mmol) and sodium borohydride (23 mg, 0.62 mmol) were dissolved in THF (40 mL), and added to the reaction mixture, and the mixture was stirred at room temperature. After progression of the reaction was confirmed by thin layer chromatography (developing solvent: ethyl acetate/n-hexane=2/1), the reaction mixture was added with purified water, and then added with saturated brine, and the aqueous layer was separated from the THF layer. The aqueous layer was extracted 5 times with ethyl acetate, the organic layer was mixed with the THF layer, and this organic solvent layer was dried over anhydrous sodium sulfate, then concentrated under reduced pressure. The residue was purified by silica gel chromatography (developing solvent: ethyl acetate/n-hexane=1/8 to 1/6) to obtain Compound 5 (66 mg, 29% yield).

$^1$H-NMR (300 MHz, CDCl$_3$) δ 2.94 (d, 3H, J=5.1 Hz), 4.27 (br, 1H), 6.88 (dd, 1H, J=2.4, 8.9 Hz), 6.92 (d, 1H, J=2.4 Hz), 7.92 (d, 1H, J=8.9 Hz). $^{13}$C-NMR (75 MHz, CDCl$_3$) δ 30.4, 99.2, 113.9, 116.8, 125.4, 129.5, 138.8, 144.6, 149.9. MS (EI$^+$) 189, M$^+$.

(E) Synthesis of N-methylaminoluciferin (10)

D-Cysteine hydrochloride monohydrate (102 mg, 0.58 mmol) was dissolved in purified water degassed with argon, and its pH was adjusted to 7.9 with a 0.5 mol/L potassium carbonate solution to prepare D-cysteine solution. Compound 4 (45 mg, 0.24 mmol) was dissolved in methanol (15 mL) degassed with argon, and added with the D-cysteine solution. After argon substitution, the mixture was stirred at room temperature under light shielding condition. The reaction mixture's pH was adjusted to about 4 by adding several drops of hydrochloric acid, and methanol was evaporated. The remaining aqueous layer was extracted 3 times with ethyl acetate. The organic layer was washed with saturated brine, dried over anhydrous sodium sulfate, and concentrated under reduced pressure. The residue was purified by preparative HPLC (Eluent A=water/0.1% trifluoroacetic acid, Eluent B=80% acetonitrile/20% water/0.1% trifluoroacetic acid, A/B=80/20 to 20/80 (20 minutes)) (54 mg, 78% yield) and recrystallized from ethanol/n-hexane to obtain Compound 10. M.p. 132-134° C. (dec.).

$^1$H-NMR (300 MHz, CD$_3$OD) δ 2.84 (s, 3H), 3.67-3.78 (m, 2H), 5.35 (t, 1H, J=9.1 Hz), 6.88 (dd, 1H, J=2.3, 9.0 Hz), 6.99 (d, 1H, J=2.3 Hz), 7.75 (d, 1H, J=9.0 Hz). $^{13}$C-NMR (75 MHz, CD$_3$OD) δ 32.0, 35.8, 79.2, 104.3, 118.0, 125.7, 140.0, 147.9, 148.5, 157.0, 167.9, 173.3. HRMS (ESI$^+$) Calcd for [M+H]$^+$: 294.0371, Found: 294.0340.

Anal. Calcd for C$_{12}$H$_{11}$N$_3$O$_2$S$_2$·0.25H$_2$O: C, 48.4; H, 3.9; N, 14.1, Found: C, 48.5; H, 4.2; N, 13.7.

(F) Synthesis of 2-cyano-N-dimethylaminobenzothiazole (6)

Formaldehyde (37% (v/v), 390 mg, 4.85 mmol) was dissolved in tetrahydrofuran (THF, 20 mL), and added with 180 mmol/L sulfuric acid (3.7 mL, 0.7 mmol), and the mixture was stirred at room temperature for several minutes. Compound 4 (119 mg, 0.68 mmol) and sodium borohydride (26 mg, 0.70 mmol) were dissolved in THF (40 mL), and added to the reaction mixture, and the mixture was stirred at room temperature. After progression of the reaction was confirmed by thin layer chromatography (developing solvent: ethyl acetate/n-hexane=2/1), the reaction mixture was added with purified water, then added with saturated brine, and the aqueous layer was separated from the THF layer. After the aqueous layer was extracted 5 times with ethyl acetate, the organic layer was mixed with the THF layer, dried over anhydrous sodium sulfate, and concentrated under reduced pressure. The residue was purified by silica gel chromatography (developing solvent: ethyl acetate/n-hexane =1/6 to 1/4) to obtain Compound 6 (74 mg, 54% yield).

$^1$H-NMR (300 MHz, CDCl$_3$) δ 3.10 (s, 6H), 7.01 (d, 1H, J=2.6 Hz), 7.06 (dd, 1H, J=2.6, 9.2 Hz), 7.98 (d, 1H, J=9.2 Hz).

$^{13}$C-NMR (75 MHz, CDCl$_3$) δ 40.6, 100.7, 114.0, 114.8, 125.1, 129.4, 138.6, 143.8, 150.6. MS (EI$^+$) 203, M$^+$.

(G) Synthesis of N,N-dimethylaminoluciferin (11)

The titled compound was synthesized in the same manner as Compound 10 mentioned above.

M.p. 177-178° C. (dec.).

$^1$H-NMR (300 MHz, DMSO-d$_6$) δ 3.10 (s, 6H), 3.70 (dd, 1H, J=8.3, 11.4 Hz), 3.81 (dd, 1H, J=9.6, 11.4 Hz), 5.44 (dd,

1H, J=8.3, 9.6 Hz), 7.14 (dd, 1H, J=2.5, 9.3 Hz), 7.38 (d, 1H, J=2.5 Hz), 7.98 (d, 1H, J=9.3 Hz), 13.22 (br, 1H).
$^{13}$C-NMR (75 MHz, acetone-d$_6$) δ 35.3, 41.0, 79.2, 103.0, 115.0, 125.3, 139.5, 146.1, 150.9, 156.0, 166.2, 171.5. HRMS (ESI$^+$) Calcd for [M+H]$^+$: 308.0527, Found: 308.0481.
Anal. Calcd for C$_{13}$H$_{13}$N$_3$O$_2$S$_2$: C, 50.8; H, 4.3; N, 13.7, Found: C, 50.6; H, 4.4; N, 13.4.

(H) Synthesis of 2-cyano-6-benzylaminobenzothiazole (7)
The titled compound was synthesized in the same manner as in Compound 5 mentioned above.
$^1$H-NMR (300 MHz, CDCl$_3$) δ 4.43 (d, 2H, J=5.6 Hz), 4.61 (br, 1H), 6.91-6.97 (m, 2H), 7.30-7.39 (m, 5H), 7.93 (d, 1H, J=9.7 Hz).
$^{13}$C-NMR (75 MHz, CDCl$_3$) δ 48.0, 100.2, 113.8, 117.0, 125.5, 127.3, 127.7, 128.9, 129.9, 137.7, 138.6, 144.8, 148.7. HRMS (ESI$^+$) Calcd for [M+H]$^+$: 266.0752, Found: 266.0759.

(I) Synthesis of N-benzylaminoluciferin (12)
The titled compound was synthesized in the same manner as Compound 10 mentioned above.
M.p. 108-109° C. (dec.).
$^1$H-NMR (300 MHz, CD$_3$OD) δ 3.66-3.78 (m, 2H), 4.41 (s, 2H), 5.34 (t, 1H, J=9.1 Hz), 6.97 (dd, 1H, J=2.2, 8.9 Hz), 7.02 (d, 1H, J=2.2 Hz), 7.20-7.41 (m, 5H), 77.77(d, 1H, J=8.9 Hz).
$^{13}$C-NMR (75 MHz, CD$_3$OD) δ 35.7, 48.9, 79.1, 102.9, 117.5, 125.5, 128.2, 128.5, 129.6, 139.9, 140.0, 146.7, 149.3, 155.8, 167.9, 173.3. HRMS (ESI$^+$) Calcd for [M+H]$^+$: 370.0684, Found: 370.0683.
Anal. Calcd for C$_{18}$H$_{15}$N$_3$O$_2$S$_2$·0.5H$_2$O: C, 57.1; H, 4.3; N, 11.1, Found: C, 57.1; H, 4.5; N, 10.7.

(J) Synthesis of 2-cyano-6-phenylaminobenzothiazole (8)
The titled compound was synthesized in the same manner as Compound 5 mentioned above.
$^1$H-NMR (300 MHz, CDCl$_3$) δ 2.98 (t, 2H, J=6.9 Hz), 3.49 (td, 2H, J=5.9, 6.9 Hz), 4.22 (br, 1H), 6.85 (dd, 1H, J=2.4, 9.0 Hz), 6.95 (d, 1H, J=2.4 Hz), 7.21-7.38 (m, 5H) 7.91 (d, 1H, J=9.0 Hz).
$^{13}$C-NMR (75 MHz, CDCl$_3$) δ 34.9, 44.6, 99.8, 113.8, 117.0, 125.4, 126.6, 128.6, 128.6, 129.5, 138.4, 138.6, 144.6, 148.7. HRMS (ESI$^+$) Calcd for [M+H]$^+$: 280.0908, Found: 280.0876.

(K) Synthesis of N-phenethylaminoaminoluciferin (13)
The titled compound was synthesized in the same manner as Compound 10 mentioned above.
$^1$H-NMR (300 MHz, CD$_3$OD) δ 2.94 (t, 2H, J=7.3 Hz), 3.45 (t, 2H, J=7.3 Hz), 3.68-3.79 (m, 2H), 5.36 (t, 1H, J=9.0 Hz), 6.94 (dd, 1H, J=2.3, 9.0 Hz), 7.13 (d, 1H, J=2.3 Hz), 7.19-7.31 (m, 5H), 7.79 (d, 1H, J=9.0 Hz).
$^{13}$C-NMR (75 MHz, CD$_3$OD) δ 35.8, 35.9, 47.0, 79.0, 103.2, 117.6, 125.6, 127.4, 129.5, 129.8, 140.1, 140.5, 147.0, 148.6, 156.0, 167.9, 173.3. HRMS (ESI$^+$) Calcd for [M+H]$^+$: 384.0840, Found: 384.0816.

(L) Synthesis of 2-cyano-6-phenylpropylaminobenzothiazole (9)
The titled compound was synthesized in the same manner as Compound 5 mentioned above.
$^1$H-NMR (300 MHz, CDCl$_3$) δ 2.02 (tt, 2H, J=7.2, 7.4 Hz), 2.77 (t, 2H, J=7.4 Hz), 3.22 (td, 2H, J=5.7, 7.2 Hz), 4.15 (br, 1H), 6.79-6.84 (m, 2H), 7.19-7.36 (m, 5H), 7.89 (d, 1H, J=9.5 Hz). $^{13}$C-NMR (75 MHz, CDCl$_3$) δ 30.4, 33.2, 43.0, 99.6, 113.9, 117.0, 125.4, 126.1, 128.3, 128.5, 129.5, 138.7, 141.0, 144.5, 148.9. HRMS (ESI$^+$) Calcd for [M+H]$^+$: 294.1065, Found: 294.1091.

(M) Synthesis of N-phenylpropylaminoluciferin (14)
The titled compound was synthesized in the same manner as Compound 10 mentioned above.
M.p. 128-129° C. (dec.). $^1$H-NMR (300 MHz, CD$_3$OD) δ 1.88 (tt, 2H, J=7.3, 7.5 Hz), 2.65 (t, 2H, J=7.5 Hz), 3.11 (t, 2H, J=7.3 Hz), 3.58-3.70 (m, 2H), 5.27 (t, 1H, J=9.0 Hz), 6.87 (dd, 1H, J=2.4, 9.0 Hz), 6.98 (d, 1H, J=2.4 Hz), 7.12-7.22 (m, 5H), 7.71 (d, 1H, J=9.0 Hz). $^{13}$C-NMR (75 MHz, CD$_3$OD) δ 31.2, 34.1, 35.8, 45.4, 79.1, 101.9, 104.0, 118.0, 125.6, 127.0, 129.4, 140.0, 142.8, 147.4, 147.9, 156.5, 167.8, 173.3. HRMS (ESI$^+$) Calcd for [M+H]$^+$: 398.0997, Found: 398.0959.
Anal. Calcd for C$_{20}$H$_{19}$N$_3$O$_2$S$_2$: C, 60.4; H, 4.8; N, 10.6, Found: C, 60.4; H, 4.9; N, 10.4.

Example 2

Measurement of luminescence spectra of luciferin, aminoluciferin and Compounds 10 to 14

Figure 1:
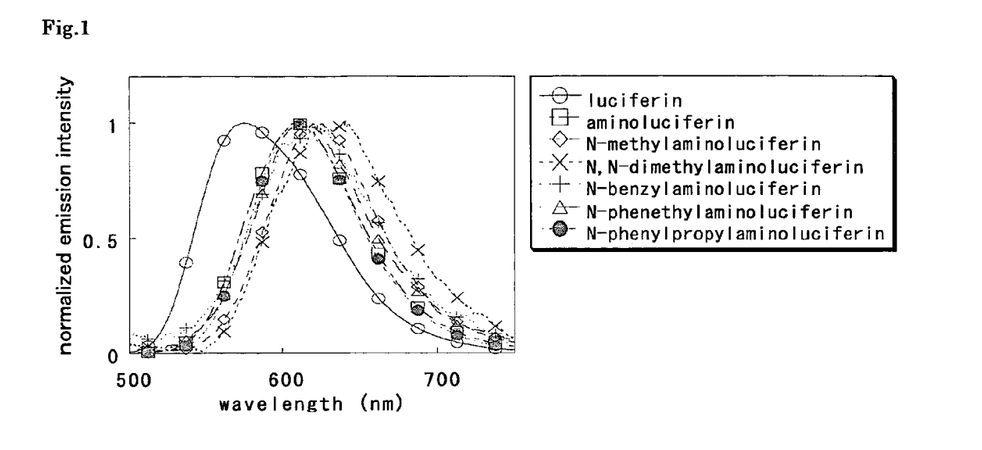
FIG. 1 shows measured luminescence spectra of the compounds of the present invention.

Luminescence spectra of luciferin, aminoluciferin and Compounds 10 to 14 were measured. To measure luminescence spectra, agents were dissolved in 30 mmol/L N-2-hydroxyethylpiperazine-N'-2-ethanesulfonic acid (HEPES) buffer (pH 7.7) so that the solution contained 5 mmol/L magnesium sulfate, 2.6 mmol/L adenosine triphosphate (ATP), 3.5 mmol/L dithiothreitol (DTT), 1.5 mmol/L coenzyme A (CoA) and 20 or 40 µg/mL luciferase (firefly, 20 µg/mL for luciferin, 40 µg/mL for aminoluciferin and Compounds 10 to 14), and finally to the solution was added each luciferin (containing 0.2% DMSO as cosolvent (except for luciferin)) at a final concentration of 6 or 12 µmol/L (6 µmol/L of luciferin, 12 µmol/L of aminoluciferin and Compounds 10 to 14). Spectra were standardized on the basis of the peak top of each luciferin. The measurement was performed by using Fluorescence Spectrophotometer F-4500 (Hitachi). The results are shown in FIG. 1. Luminescent property was observed for every compound of the present invention, Compounds 10 to 14, in which the amino group of aminoluciferin was alkylated. Further, the luminescence spectra thereof were significantly shifted to the long wavelength side compared with that of luciferin.

Example 3

Luminescence characteristics of luciferin, aminoluciferin and Compounds 10 to 14

Luminescence characteristics of luciferin, aminoluciferin and Compounds 10 to 14 were evaluated. To measure luminescence, agents were dissolved in 30 mmol/L HEPES buffer (pH 7.7) so that the solution contained 5 mmol/L magnesium sulfate, 2.6 mmol/L ATP, 3.5 mmol/L DTT, 1.5 mmol/L CoA and 20 µg/mL luciferase (firefly), and to the solution was finally added each luciferin (containing 0.2% DMSO as a cosolvent (except for luciferin)) at a final concentration of 12 µmol/L. Relative intensity was calculated on the basis of the intensity obtained for aminoluciferin. The measurement was performed by using Fluorescence Spectrophotometer F-4500 (Hitachi). The results are shown in Table 1.

TABLE 1

|  | λmax(nm) | initial intensity | relative intensity |
|---|---|---|---|
| luciferin | 575 | 7332 |  |
| aminoluciferin | 609 | 2044 | 100.0 |

TABLE 1-continued

|  | λmax(nm) | initial intensity | relative intensity |
| --- | --- | --- | --- |
| N-methylaminoluciferin | 624 | 1360 | 66.5 |
| N,N-dimethylaminoluciferin | 641 | 901 | 44.1 |
| N-benzylaminoluciferin | 623 | 106 | 5.2 |
| N-phenethylaminoluciferin | 611 | 175 | 8.6 |
| N-phenylpropylaminoluciferin | 611 | 980 | 48.0 |

Luminescent property was observed for every compound of the present invention, Compounds 10 to 14, in which the amino group of aminoluciferin was alkylated. Although the luminescence intensities thereof were lower than that of aminoluciferin, the peak luminescence wavelengths were observed on the longer wavelength side compared with that of luciferin by 34 nm for aminoluciferin, 49 nm for Compound 10, 66 nm for Compound 11, 48 nm for Compound 12, 36 nm for Compound 13, and 36 nm for Compound 14. That is, luminescence wavelengths of the compounds of the present invention, Compounds 10 to 14, all shifted to the longer wavelength side compared with those of luciferin and aminoluciferin.

Example 4

Synthesis of phenethylaminoluciferin derivatives

The synthetic scheme for Compounds 19 and 21 is shown below.

water, then dried over anhydrous sodium sulfate, then concentrated under reduced pressure. The residue was purified by silica gel column chromatography (developing solvent: ethyl acetate/n-hexane=1/2 to 1/1) to obtain Compound 16 (2.36 g, 61% yield).

$^1$H-NMR (300 MHz, CDCl$_3$) δ 1.36 (t, 1H, J=6.1 Hz), 2.83 (t, 2H, J=6.5 Hz), 3.83 (td, 2H, J=6.1, 6.5 Hz), 5.20 (s, 2H), 6.63 (br, 1H), 7.17 (td, 2H, J=2.2, 8.4 7.29-7.44 (m, 7H).

$^{13}$C-NMR (75 MHz, CDCl3) δ 38.4, 63.6, 67.0, 119.1, 128.2, 128.3, 128.6, 129.6, 133.7, 136.0, 136.2, 153.4. HRMS (ESI$^+$) Calcd for [M+Na]$^+$: 294.1106, Found: 294.1097.

(B) Synthesis of 4-benzyloxycarbonylamidophenylacetaldehyde (17)

Compound 16 (2.36 g, 8.71 mmol) was dissolved in dichloromethane, added with magnesium sulfate, and stirred at room temperature for several minutes. The mixture was added with pyridinium chlorochromate (PCC, 3.20 g, 14.8 mmol), and stirred at room temperature. Progression of the reaction was confirmed by thin layer chromatography (developing solvent: ethyl acetate/n-hexane=2/1), and then the solid in the reaction mixture was removed by Celite filtration. The residue was purified by silica gel chromatography (developing solvent: ethyl acetate/n-hexane=1/6 to 1/4) to obtain Compound 17 (299 mg, 13% yield).

$^1$H-NMR (300 MHz, CDCl$_3$) δ 3.65 (d, 2H, J=2.2 Hz), 5.21 (s, 2H), 6.65 (br, 1H), 7.16 (td, 2H, J=2.2, 8.4 Hz), 7.34-7.45 (m, 7H), 9.72 (t, 1H, J=2.2 Hz). $^{13}$C-NMR (75 MHz, CDCl$_3$)

(A) Synthesis of 4-benzyloxycarbonylamidophenetyl alcohol (16)

Compound 15 (1.97 g, 14.4 mmol) was dissolved in THF (50 mL) dehydrated with molecular sieve, and the solution was added with triethylamine (2 mL, 14 mmol), and stirred at room temperature for several minutes. Then, the mixture was carefully added with benzyloxyearbonyl chloride (2.5 mL, 17 mmol), and stirred overnight at room temperature. Progression of the reaction was confirmed by thin layer chromatography (developing solvent: ethyl acetate/n-hexane=2/1), and then THF was evaporated. After dissolving the residue in dichloromethane, the solution was washed with purified δ 49.5, 66.6, 119.0, 126.3, 127.9, 128.0, 128.3, 129.9, 135.8, 137.1, 153.4, 199.6. HRMS (ESI$^+$) Calcd for [M+Na]$^+$: 292.0950, Found: 292.0954.

(C) Synthesis of 2-cyano-6-(4'-benzyloxycarbonylamidophenethyl)-aminobenzothiazole (18)

Compound 17 (376 mg, 1.40 mmol) was dissolved in THF (70 mL), and the solution was added with 180 mmol/L sulfuric acid (8 mL, 1.4 mmol), and stirred at room temperature for several minutes. The mixture was added with Compound 4 and sodium borohydride (54 mg, 1.43 mmol) dissolved in THF (60 mL) were added to mixture, and stirred at room temperature. After progression of the reaction was confirmed by thin layer chromatography (developing solvent: ethyl acetate/n-hexane=2/1), the reaction mixture was added with purified water and added with saturated brine, then the aqueous layer was separated from the THF layer. After the aqueous layer was extracted 5 times with ethyl acetate, the organic layer was mixed with the THF layer, dried over anhydrous sodium sulfate, and concentrated under reduced pressure. The residue was purified twice by silica gel chromatography (developing solvent: ethyl acetate/n-hexane=1/6 to 1/4 to 1/2) to obtain Compound 18 (157 mg, 29% yield).

$^1$H-NMR (300 MHz, CDCl3) δ 2.93 (t, 2H, J=6.9 Hz), 3.45 (td, 2H, J=6.1, 6.9 Hz), 4.19 (br, 1H), 5.20 (s, 2H), 6.66 (br, 1H), 6.83 (dd, 1H, J=2.3, 9.0 Hz), 6.93 (d, 1H, J=2.3 Hz), 7.16 (td, 2H, J=1.8, 8.4 Hz), 7.29-7.43 (m, 7H), 7.90 (d, 1H, J=9.0 Hz). 13C-NMR (75 MHz, CDCl$_3$) δ 34.2, 44.6, 66.8, 99.8, 113.8, 116.9, 119.1, 125.3, 127.9, 128.1, 128.2, 128.4, 129.1, 133.5, 135.9, 136.4, 138.6, 144.5, 148.7, 153.4. HRMS (ESI$^+$) Calcd for [M+Na]$^+$: 451.1205, Found: 451.1243.

(D) Synthesis of 6-(4'-benzyloxycarbonylamidophenethyl)-aminoluciferin (19)

D-Cysteine hydrochloride monohydrate (58 mg, 0.33 mmol) was dissolved in purified water degassed with argon, and its pH was adjusted to 8.1 with a 0.5 mol/L potassium carbonate solution to prepare a D-cysteine solution. Compound 18 (58 mg, 0.14 mmol) was dissolved in methanol (15 mL) degassed with argon, and added with the D-cysteine solution. After argon substitution, the mixture was stirred at room temperature with light shielding. The reaction mixture was adjusted to about pH 4 with addition of several drops of hydrochloric acid, then methanol was evaporated. After the remaining aqueous layer was extracted 3 times with ethyl acetate, and the organic layer was washed with saturated brine, dried over anhydrous sodium sulfate, and concentrated under reduced pressure. The residue was purified by preparative HPLC (EluentA=water/0.1% trifluoroacetic acid, Eluate B=80% acetonitrile/20% water/0.1% trifluoroacetic acid, A/B=50/50 to 0/100 (20 minutes)) to obtain Compound 19 (59 mg, 81% yield).

$^1$H-NMR (300 MHz, CD$_3$OD) δ 2.80 (t, 2H, J=7.4 Hz), 3.35 (t, 2H, J=7.4 Hz), 3.58-3.71 (m, 2H), 5.06 (s, 2H), 5.27 (t, 1H, J=9.0 Hz), 6.91 (dd, J=2.0, 9.0 Hz), 7.05-7.13 (m, 3H), 7.17-7.33 (m, 7H), 7.73 (d, 1H, J=9.0 Hz).

$^{13}$C-NMR (75 MHz, CD$_3$OD) δ 35.2, 35.3, 45.8, 66.8, 79.1, 101.5, 116.5, 119.3, 125.4, 128.8, 128.9, 129.3, 130.0, 134.8, 137.9, 138.3, 139.8, 146.1, 149.7, 154.3, 155.0, 166.3, 171.5. HRMS (ESI$^+$), Calcd for [M+H]$^+$: 533.1317, Found: 533.1365.

(E) Synthesis of 2-cyano-6-(4'-aminophenethyl)-aminobenzothiazole (20)

Compound 18 (92 mg, 0.22 mmol) was dissolved in dichloromethane (10 mL), and the solution was added with trifluoroacetic acid (60 mL). The mixture was stirred overnight at room temperature, then refluxed at 60° C. After disappearance of the starting materials was confirmed by thin layer chromatography (developing solvent: ethyl acetate/n-hexane=2/1), the reaction mixture was evaporated, and trifluoroacetic acid was removed azeotropically with toluene. The residue was dissolved in ethyl acetate, and the solution was washed with purified water and saturated brine, then dried over anhydrous sodium sulfate, and concentrated under reduced pressure. The residue was purified by silica gel column chromatography (developing solvent: ethyl acetate/n-hexane=1/3 to 1/2 to 1/1 to 2/1) to obtain Compound 20 (42 mg, 67% yield).

$^1$H-NMR (300 MHz, CDCl$_3$) δ 2.86 (t, 2H, J=6.8 Hz), 3.41 (t, 2H, J=6.8 Hz), 6.66 (td, 2H, J=2.0, 8.4 Hz), 6.83 (dd, 1H, J=2.2, 9.0 Hz), 6.93 (d, 1H, J=2.2 Hz), 7.01 (td, 2H, J=2.0, 8.4 Hz), 7.89 (d, 1H, J=9.0 Hz). $^{13}$C-NMR (75 MHz, CDCl$_3$) δ 34.1, 44.9, 99.9, 113.8, 115.4, 117.0, 125.4, 128.1, 129.5, 138.7, 144.7, 145.0, 148.9. HRMS (ESI$^+$) Calcd for [M+H]$^+$: 295.1017, Found: 295.1005.

(F) Synthesis of 6-(4'-aminophenethyl)-aminoluciferin (21)

D-Cysteine hydrochloride monohydrate (64 mg, 0.36 mmol) was dissolved in purified water degassed with argon, and its pH was adjusted to 8.2 with a 0.5 mol/L potassium carbonate solution to prepare a D-cysteine solution. Compound 20 (42 mg, 0.14 mmol) was dissolved in methanol (15 mL) and ethanol (15 mL) degassed with argon, and the solution was added with the D-cysteine solution. After argon substitution, the mixture was stirred at room temperature with light shielding. The reaction mixture's pH was adjusted to about 4 with several drops of hydrochloric acid, and methanol and ethanol were evaporated. After the remaining aqueous layer was extracted 3 times with ethyl acetate, and the organic layer was washed with saturated brine, dried over anhydrous sodium sulfate, and concentrated under reduced pressure. The residue was purified twice by preparative HPLC (Eluent A=water/0.1% trifluoroacetic acid, Eluent B=80% CH$_3$CN/20% water/0.1% trifluoroacetic acid, A/B=80/20 to 20/80 (20 minutes)) to obtain Compound 21 (26 mg, 46% yield).

$^1$H-NMR (300 MHz, CD$_3$OD) δ 2.84 (t, 2H, J=7.2 Hz), 3.33 (t, 2H, J=7.2 Hz), 3.57-3.68 (m, 2H), 5.25 (t, 1H, J=9.1 Hz), 6.77 (dd, 1H, J=2.3, 9.0 Hz), 6.92 (d, 1H, J=2.3 Hz), 7.04 (td, 2H, J=1.8, 8.4 Hz), 7.23 (td, 2H, J=1.8, 8.4 Hz), 7.64 (d, 1H, J=9.0 Hz). $^{13}$C-NMR (75 MHz, acetone-d$_6$) δ 35.3, 46.2, 79.2, 101.3, 115.4, 116.5, 120.5, 125.4, 128.4, 130.1, 139.8, 146.0, 147.5, 149.8, 154.9, 166.2, 171.6. HRMS (ESI$^+$) Calcd for [M+H]$^+$: 399.0949, Found: 399.0914

Example 5

Measurement of luminescence of Compounds 19 and 20

Figure 2:
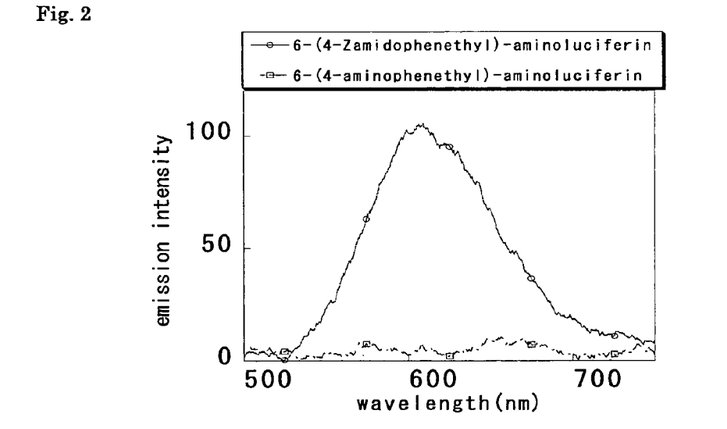
FIG. 2 shows measured luminescence spectra of Compounds 19 and 21 of the present invention after reaction with a luciferase.

Luminescence spectra of Compounds 19 and 20 were measured. To measure luminescence, agents were dissolved in 30 mmol/L HEPES buffer (pH 7.7) so that the solution should contain 5 mmol/L magnesium sulfate, 2.6 mmol/L ATP, 3.5 mmol/L DTT, 1.5 mmol/L CoA and 40 μg/mL luciferase (firefly), and the solution was finally added with each luciferin (containing 0.2% DMSO as a cosolvent) at a final concentration of 12 μmol/L. The measurement was performed by using Fluorescence Spectrophotometer F-4500 (Hitachi). The results are shown in FIG. 2. Compound 19 showed a luminescence spectrum with a luminescence peak at about 610 nm, whereas Compound 21 completely lost the luminescent property.

Example 6

HPLC analysis of luciferase reaction product of Compound 21

Figure 3:
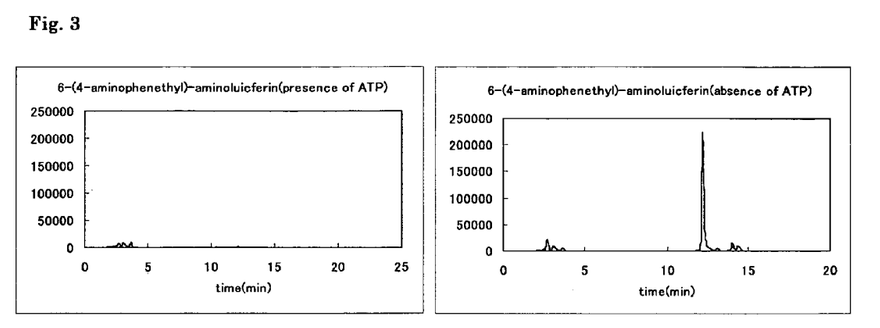
FIG. 3 shows results of HPLC analyses for Compound 21 of the present invention reacted with a luciferase in the presence or absence of ATP.

For 6-(4-aminophenethyl)-aminoluciferin (Compound 21), the enzymatic reaction was also performed in a system without ATP (all the other conditions were the same as Example 5), along with the aforementioned enzymatic reaction in Example 5. After these two enzymatic reactions, each enzymatic reaction mixture was collected and filtered by using a centrifugal separator to remove the enzyme. The solvent was evaporated by lyophilization to obtain a residue after the enzymatic reaction. A small amount of the residue was dissolved in purified water and methanol, then analyzed by HPLC. The results are shown in FIG. 3.

Analysis conditions

Elution solvent: A=H$_2$O/0.1% trifluoroacetic acid, B=80% acetonitrile/20% water/0.1% trifluoroacetic acid, A/B=80/20 to 20/80 (20 minutes)

Detection: UV-vis (400 nm)

Column: ODS-3, 4.6×250 mm

Flow rate: 1 mL/min

The HPLC analysis of the luciferase (firefly) reaction product of Compound 21, the peak of Compound 21 was observed at about 12 minutes in the reaction system without ATP. This is because the luciferin-luciferase reaction requires ATP as a cofactor, and no enzymatic reaction occurs in a system without ATP. On the other hand, no elution peak of Compound 21 was observed in the system added with ATP. More specifically, it was confirmed that Compound 21 reacted as a luciferase substrate. This result and the results of Example 5 suggest that, although Compound 21 reacts with luciferase, electrons of the amino group-substituted benzene ring moiety with high electron density (high HOMO energy) were donated to the aminoluciferin moiety as the luminescent moiety, and the luminescence process as a result of the reaction with luciferase was quenched, and also that, on the other hand, Compound 19 with an acylated amino group has electron density of the amino group-substituted benzene ring moiety, thus electron donation to the aminoluciferin moiety did not occur, and luminescence was observed.

What is claimed is:

1. A compound represented by the following general formula (I) or a salt thereof:

(I)

[wherein $R^1$ and $R^2$ independently represent hydrogen atom, a $C_{1-6}$ alkyl group which may be substituted, or a group represented by the following formula (A):

(A)

[wherein $X^1$ and $X^2$ independently represent hydrogen atom, or a group represented as —N($R^3$)($R^4$) (wherein $R^3$ and $R^4$ independently represent hydrogen atom, a $C_{1-6}$ alkyl group which may be substituted, a $C_{1-6}$ alkylcarbonyl group which may be substituted, or a $C_{1-6}$ alkyloxycarbonyl group which may be substituted); and n represents an integer of 1 to 6], provided that $R^1$ and $R^2$ do not simultaneously represent hydrogen atom].

2. The compound or a salt thereof according to claim 1, wherein either one of $R^1$ and $R^2$ is hydrogen atom, and the other is a group represented by the formula (A), and in the formula (A), $X^1$ and $X^2$ both are hydrogen atoms, and n is an integer of 1 to 6.

3. The compound or a salt thereof according to claim 1, wherein either one of $R^1$ and $R^2$ is hydrogen atom, and the other is a group represented by the formula (A), and in the formula (A), $X^1$ is hydrogen atom, and $X^2$ is a group represented as —N($R^3$)($R^4$), wherein $R^3$ and $R^4$ independently represent hydrogen atom, or a $C_{1-6}$ alkyl group which may be substituted.

4. The compound or a salt thereof according to claim 1, wherein either one of $R^1$ and $R^2$ is hydrogen atom, and the other is a group represented by the formula (A), and in the formula (A), $X^1$ is hydrogen atom, and $X^2$ is a group represented as —N($R^3$)($R^4$), wherein either one of $R^3$ and $R^4$ is hydrogen atom, and the other is a $C_{1-6}$ alkylcarbonyl group which may be substituted, or a $C_{1-6}$ alkyloxycarbonyl group which may be substituted.

5. A luciferase substrate comprising a compound represented by the general formula (I).

* * * * *